(12) United States Patent
Lin et al.

(10) Patent No.: US 7,300,637 B2
(45) Date of Patent: Nov. 27, 2007

(54) STERILIZATION CONTAINER KIT (75) Inventors: Szu-Min Lin, Laguna Hills, CA (US); Harold R. Williams, San Clemente, CA (US); Robert Lukasik, Lake Elsinore, CA (US)

(73) Assignee: Ethicon, Inc., Somerville, NJ (US)

( * ) Notice: Subject to any disclaimer, the term of this patent is extended or adjusted under 35 U.S.C. 154(b) by 446 days.

(21) Appl. No.: 10/261,214

(22) Filed: Sep. 30, 2002

(65) Prior Publication Data

US 2004/0062692 A1  Apr. 1, 2004

(51) Int. Cl.
 *A61L 2/20* (2006.01)
(52) U.S. Cl. ..................... 422/292; 422/300
(58) Field of Classification Search ............... 422/292, 422/300; 220/361, 370, 371
 See application file for complete search history.

(56) References Cited

U.S. PATENT DOCUMENTS

| 4,102,055 | A |   | 7/1978  | Volk, Jr. |
| 4,169,123 | A |   | 9/1979  | Moore et al. |
| 4,169,124 | A |   | 9/1979  | Forstrom et al. |
| 4,230,663 | A |   | 10/1980 | Forstrom et al. |
| 4,337,223 | A |   | 6/1982  | Kaye |
| 4,410,492 | A |   | 10/1983 | Kaye |
| 4,643,876 | A |   | 2/1987  | Jacobs et al. |
| 4,660,803 | A | * | 4/1987  | Johnston et al. ......... 251/149.1 |
| 4,754,595 | A | * | 7/1988  | Sanderson .................... 53/425 |
| 4,756,882 | A |   | 7/1988  | Jacobs et al. |
| 4,817,800 | A |   | 4/1989  | Williams et al. |
| 4,869,286 | A |   | 9/1989  | Williams et al. |
| 4,877,624 | A | * | 10/1989 | Floyd et al. ................ 137/522 |
| 4,899,519 | A |   | 2/1990  | Williams et al. |
| 4,909,999 | A |   | 3/1990  | Cummings et al. |
| 4,913,196 | A |   | 4/1990  | Williams et al. |
| 4,915,351 | A | * | 4/1990  | Hoffman .................. 251/149.1 |
| 4,941,518 | A |   | 7/1990  | Williams et al. |
| 4,943,414 | A |   | 7/1990  | Jacobs et al. |
| 4,952,370 | A |   | 8/1990  | Cummings et al. |
| 4,956,145 | A |   | 9/1990  | Cummings et al. |
| 5,087,418 | A |   | 2/1992  | Jacob |
| 5,115,166 | A |   | 5/1992  | Campbell et al. |
| 5,252,303 | A | * | 10/1993 | Goof ......................... 422/292 |
| 5,266,275 | A |   | 11/1993 | Faddis |
| 5,286,448 | A |   | 2/1994  | Childers |
| 5,310,524 | A |   | 5/1994  | Campbell et al. |
| 5,346,075 | A |   | 9/1994  | Nichols et al. |
| 5,413,758 | A |   | 5/1995  | Caputo et al. |
| 5,413,760 | A |   | 5/1995  | Campbell et al. |

(Continued)

FOREIGN PATENT DOCUMENTS

CA  2149923 A  11/1992

(Continued)

OTHER PUBLICATIONS

European Search Report EP 00 31 1545 dated Mar. 6, 2003.*

(Continued)

*Primary Examiner*—Gladys J P Corcoran
*Assistant Examiner*—Sean Conley (57) ABSTRACT

A sterilization container holds instruments during a sterilization process. It has an enclosure with an opening into the enclosure and an adapter at the opening. Various inserts such as semi-permeable filters and blocking plates may be placed into the adapter.

10 Claims, 9 Drawing Sheets

U.S. PATENT DOCUMENTS

| | | | |
|---|---|---|---|
| 5,425,815 A | 6/1995 | Parker et al. | |
| 5,443,801 A | 8/1995 | Langford | |
| 5,451,368 A | 9/1995 | Jacob | |
| 5,492,672 A | 2/1996 | Childers et al. | |
| 5,527,508 A | 6/1996 | Childers et al. | |
| 5,534,221 A | 7/1996 | Hillebrenner et al. | |
| 5,552,115 A | 9/1996 | Malchesky | |
| 5,552,320 A | 9/1996 | Smith | |
| 5,556,607 A | 9/1996 | Childers et al. | |
| 5,580,530 A | 12/1996 | Kowatsch et al. | |
| 5,633,424 A | 5/1997 | Graves et al. | |
| 5,656,238 A | 8/1997 | Spencer et al. | |
| 5,667,753 A | 9/1997 | Jacobs et al. | |
| 5,674,450 A | 10/1997 | Lin et al. | |
| 5,711,921 A | 1/1998 | Langford | |
| 5,770,739 A | 6/1998 | Lin et al. | |
| 5,785,934 A | 7/1998 | Jacobs et al. | |
| 5,792,422 A | 8/1998 | Lin et al. | |
| 5,868,999 A | 2/1999 | Karlson | |
| 5,942,438 A | 8/1999 | Antonoplos et al. | |
| 5,961,921 A | 10/1999 | Addy et al. | |
| 5,993,754 A | 11/1999 | Lemmen et al. | |
| 6,030,579 A | 2/2000 | Addy et al. | |
| 6,145,687 A * | 11/2000 | Nichols et al. | 220/254.3 |
| 6,162,395 A | 12/2000 | Kowanko | |
| 6,174,502 B1 | 1/2001 | Addy et al. | |
| 6,193,931 B1 | 2/2001 | Lin et al. | |
| 6,193,932 B1 * | 2/2001 | Wu et al. | 422/28 |
| 6,218,189 B1 | 4/2001 | Antonoplos et al. | |
| 6,379,631 B1 * | 4/2002 | Wu | 422/300 |
| 6,436,659 B1 | 8/2002 | Hui et al. | |
| 6,715,628 B1 | 4/2004 | Nichols et al. | |
| 2003/0044333 A1 | 3/2003 | Wanselin et al. | |
| 2003/0072701 A1 | 4/2003 | Lin et al. | |
| 2003/0138347 A1 | 7/2003 | Lin | |
| 2004/0011689 A1 * | 1/2004 | Bauer | 206/439 |
| 2004/0062693 A1 | 4/2004 | Lin et al. | |

FOREIGN PATENT DOCUMENTS

| | | |
|---|---|---|
| DE | 26 23 917 A | 12/1977 |
| DE | 41 02 055 A1 | 1/1990 |
| EP | 0 207 417 A1 | 1/1987 |
| EP | 0 223 479 A2 | 5/1987 |
| EP | 0 302 418 A2 | 2/1989 |
| EP | 0 302 419 B1 | 2/1989 |
| EP | 0 302 420 A2 | 2/1989 |
| EP | 0 456 135 A | 11/1991 |
| EP | 0 799 621 A1 | 10/1997 |
| EP | 0 898 971 A2 | 3/1999 |
| EP | 0 923 951 A2 | 6/1999 |
| EP | 1 110 559 A2 | 6/2001 |
| WO | WO 94/12090 A | 11/1992 |
| WO | WO 99/27971 A2 | 6/1999 |

OTHER PUBLICATIONS

European Search Report EP 97 30 2305 dated Jul. 25, 1997.*
Korean Office Action dated Sep. 18, 2004 for Korean Application No. 10-1997-0012448.*

* cited by examiner

STERILIZATION CONTAINER KIT

FIELD OF THE INVENTION

The present invention relates to sterilization containers, and more particularly to sterilization containers that are suitable for use in multiple sterilization processes.

BACKGROUND OF THE INVENTION

Medical instruments that are being sterilized for reuse are typically sterilized within some form of sterilization container. Such containers typically comprise a box having one or more openings for allowing the passage of sterilizing media. The media are typically gaseous and may comprise steam, hydrogen peroxide or ethylene dioxide to name but a few. Such containers are typically sealed in some fashion so as to allow the sterilizating media to enter the container but not to allow contaminating microorganisms to enter.

One type of container has multiple openings and is wrapped in a material such as central supply room (CSR) wrap which is permeable to the sterilizating media yet impermeable to contaminating microorganisms. An alternative is to provide filtered ports into and out of the container, the ports having a filter media transmissive to the sterilization media and impermeable to the contaminating microorganisms. Typically the container will have some features inside to hold the instruments from moving around inside the container. For instance, a silicone mat with upwardly protruding fingers may be employed. Alternatively, various clips and attaching devices are known. Sometimes a portion of the container, on an insert for the container, is molded to accommodate a particularly instrument to be sterilized.

Since the types of sterilization processes vary, it is desirable to have a container that can accommodate different sterilization processes. One attempt to achieve such a "universal" container is disclosed in U.S. Pat. No. 6,379,631 by Wu, incorporated herein by reference, wherein it was found that liquid crystal polymers are particularly suited for use in each of steam, hydrogen peroxide, ethylene dioxide sterilization processes.

Beyond the types of sterilization media, there exists a need for a container that can be employed in different sterilization processes, not merely in a process in which the container is placed into a chamber and the sterilization media introduced into the chamber. For instance it would be desirable to also be able to use the sterilization container in a process lacking a chamber and wherein a source of sterilization media connects directly to the container with the sterilization media being introduced into the container but not into the environment surrounding the container. Further, one may desire to employ the container in a process in which the sterilization media is placed into the container with the instruments and released into a gaseous form after the container is closed. These processes are disclosed in U.S. Pat. Nos. 6,193,931 and 5,785,934, each of which is incorporated herein by reference.

SUMMARY OF THE INVENTION

A sterilization container kit, according to the present invention, for sterilizing, transporting and storing one or more medical instruments, comprises an enclosure defining an interior space adapted to house the one or more medical instruments, the enclosure being sealed against the ingress of contaminating microorganisms. An opening into the enclosure has associated therewith an adapter which can receive various inserts. At least two of the inserts are selected from the list consisting of:
 a cover for blocking the opening;
 a filter for covering the opening, the filter being permeable to vapor phase sterilants and impermeable to contaminating microorganisms;
 a screen; and
 a self-closing valve.

Preferably, the adapter comprises a flange about the opening into which fits one of the at least two inserts, and more preferably further comprises a seal surrounding the opening.

An instrument holder can be provided within the enclosure to hold the instruments from moving around within the enclosure.

Preferably, there are one or more apertures into the enclosure which are capable of being sealed. A manually operated pressure release valve can be provided to allow the container to be stored at pressures differing from ambient thereby allowing a user to check the integrity of the container seal by listening for an audible rush of air through the valve when it is opened.

Preferably, the enclosure is formed of a liquid crystal polymer suitable for use with steam, hydrogen peroxide and ethylene oxide sterilization systems.

The self closing valve preferably comprises a seat at the opening and a closing member engageable with the seat wherein when the closing member is engaged with the seat the closing member blocks fluid communication between the interior space and an environment exterior of the enclosure through the opening and wherein the self closing valve closure further comprises a biasing member urging the closing member toward the seat. The self-closing valve can further comprise an inlet for receiving a projecting member from a source of sterilant, the closing member being positioned with respect to the inlet such that when the projecting member is inserted into the inlet the projecting member abuts the closing member and moves it away from the seat.

The closing member can have thereon a first flange engageable by a second flange on the projecting member whereby movement of the projecting member relative to the inlet moves the closing member.

An instrument opening into the enclosure allows for placing the one or more medical instruments therein and a lid seals the instrument opening.

DETAILED DESCRIPTION

Figure 1:
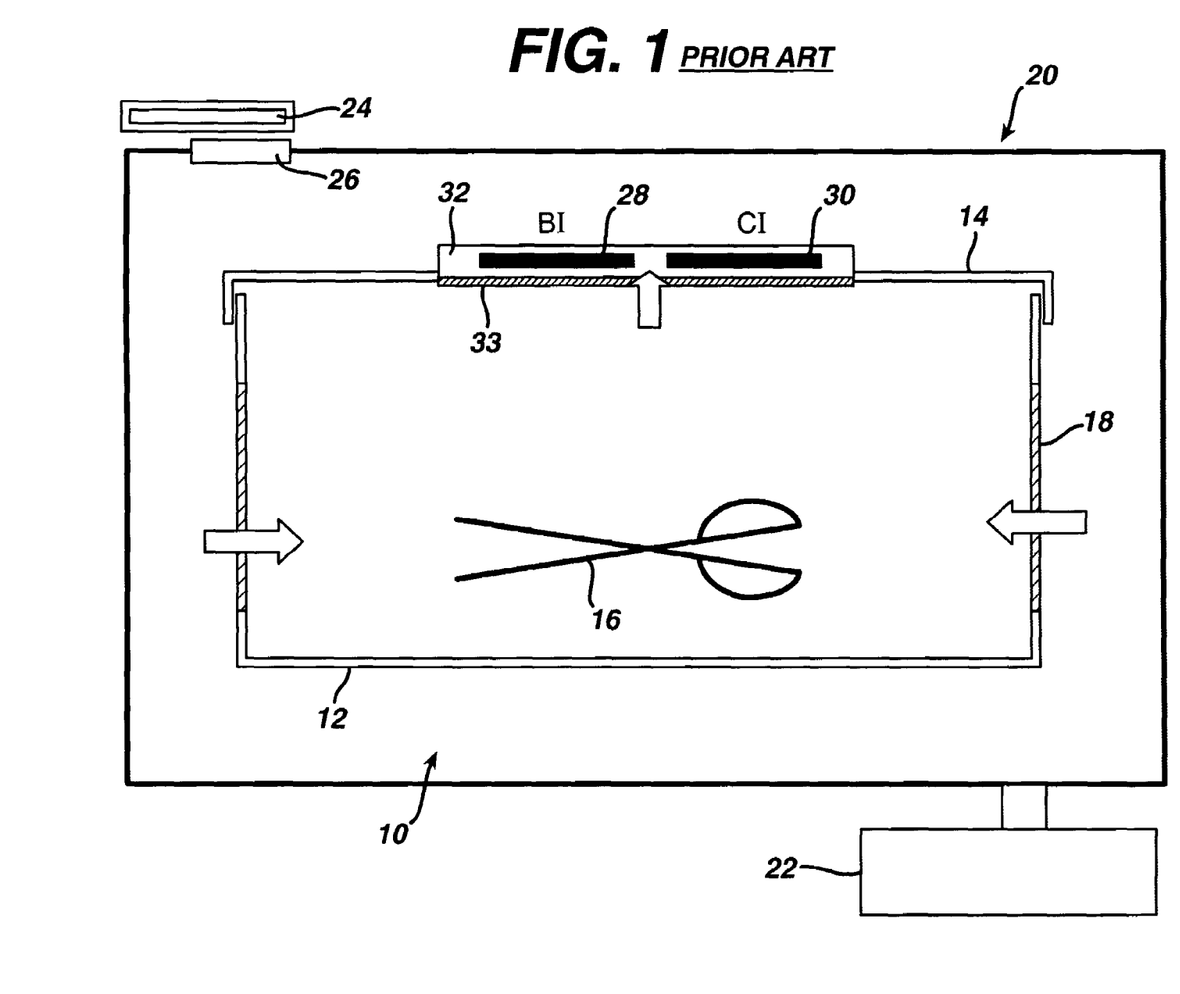
FIG. 1 is a block diagram of a prior art sterilization container in a sterilization chamber.

FIG. 1 discloses a prior art sterilization container 10 comprising an enclosure 12 having a lid 14 and containing an instrument 16 to be sterilized. Semipermeable filtered ports 18 allow sterilizating media such as steam, hydrogen peroxide vapor or ethylene oxide to enter the enclosure 12 yet prevent ingress of contaminating microorganisms after the sterilization procedure is complete. The container 10 is enclosed within a sterilization chamber 20 that comprises a vacuum pump 22 for drawing a vacuum on the chamber 20 and a cassette 24 loaded with charges of liquid hydrogen peroxide that are vaporized by a vaporizer 26 and provide vapor phase hydrogen peroxide to the chamber 20. More detail on vapor phase hydrogen peroxide sterilization can be found in U.S. Pat. Nos. 4,756,882, 4,817,800, 4,869,286, 4,899,519, 4,913,196 and 4,941,518, each of which is incorporated herein by reference.

A biological indicator 28 and chemical indicator 30 are contained within a compartment 32, which is in fluid communication with the enclosure 12 through a semipermeable membrane 33, and which can be opened to remove the biological and chemical indicators 28 and 30 after the sterilization processes is complete without exposing the instrument 16 to potentially contaminating microorganisms. A biological indicator indicates whether a test microorganism has been successfully killed in the sterilization process and a chemical indicator indicates the presence of, and in some instances and integrated exposure to, the sterilization media. Examples of biological and chemical indicators can be found in U.S. Pat. Nos. 5,552,320, 5,942,438, 6,218,189, and 6,436,659 each of which is incorporated herein by reference.

Figure 2:
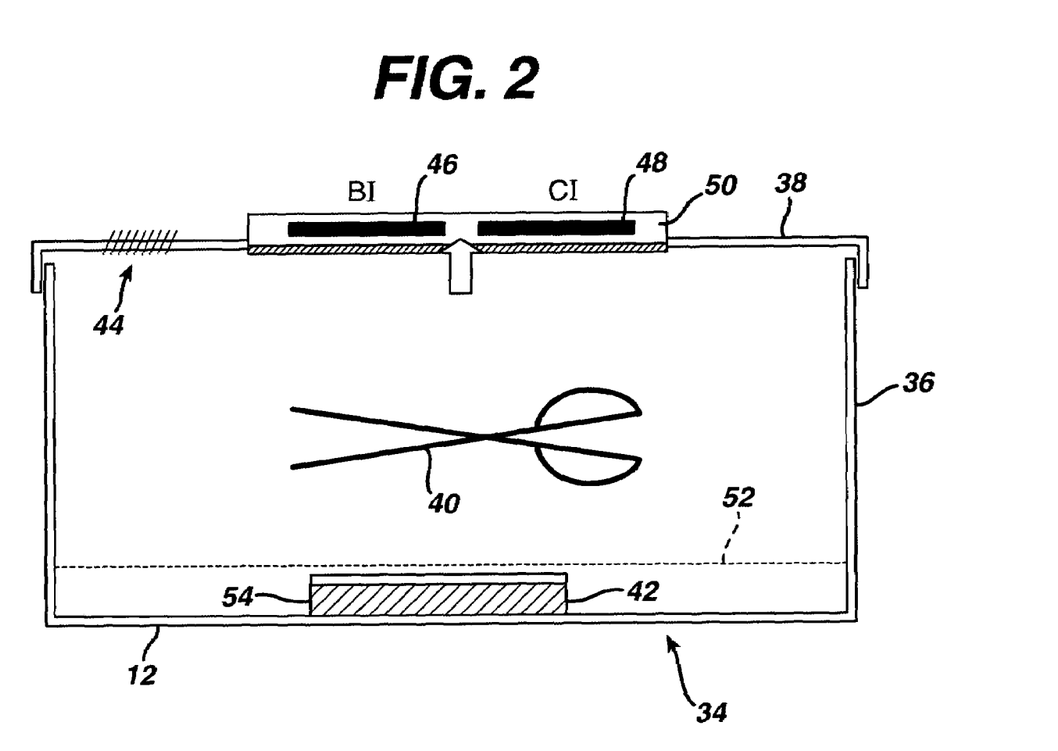
FIG. 2 is a block diagram of a self-sterilizing container.

FIG. 2 discloses a self-contained sterilization container 34 comprising an enclosure 36 having a lid 38 and containing an instrument 40 and a source of sterilant 42. At least one semipermeable port 44 is preferably provided to allow excess sterilant to exit the enclosure 36 yet prevent the ingress of contaminating microorganisms. A biological indicator 46 and chemical indicator 48 in a compartment 50, similar to the container of FIG. 1, are also provided. The source of sterilant 42 can be a solid complex that liberates a chemical sterilizing vapor, such as the urea hydrogen peroxide complexes as disclosed in U.S. Pat. Nos. 5,667,753, 5,674,450, 5,770,739 and 5,785,934, each of which is incorporated herein by reference, which liberates hydrogen peroxide when heated. Alternatively, it can be a source of liquid sterilant, such as a liquid hydrogen peroxide solution, which is vaporized. Other chemical vapor sterilants can be substituted therefore.

If the sterilant does take a liquid form it is preferably separated from the rest of the enclosure 36 by a vapor permeable membrane 52. The membrane 52 can be a part of the enclosure, or the liquid sterilant can be contained in its own enclosure 54 having the membrane 52 as a part thereof and provided with a seal either over the membrane alone 52 or enclosing the entire enclosure 54 so that in use the membrane can be unsealed and the enclosure 54 placed into the sterilization container 34 with the instrument 40. To release the sterilant, heat can be applied by heating the entire sterilization container 34, such as in an oven, or in a microwave oven. Alternatively an electric heating element can be provided within the container 34 with its wires leading exterior of the enclosure 36. In one further embodiment, the enclosure 54 that contains the sterilant can be formed of a magnetic metal and an induction element, similar to an induction element on a kitchen cook-top can be used to heat the enclosure 54 through the container 34 without unduly heating the container 34. The one or more ports 44 can be sealed during a portion of this process to keep the concentration of the sterilant within the enclosure 36 relatively high to shorten the sterilization period and ensure a more consistent sterilization process.

Figure 3:
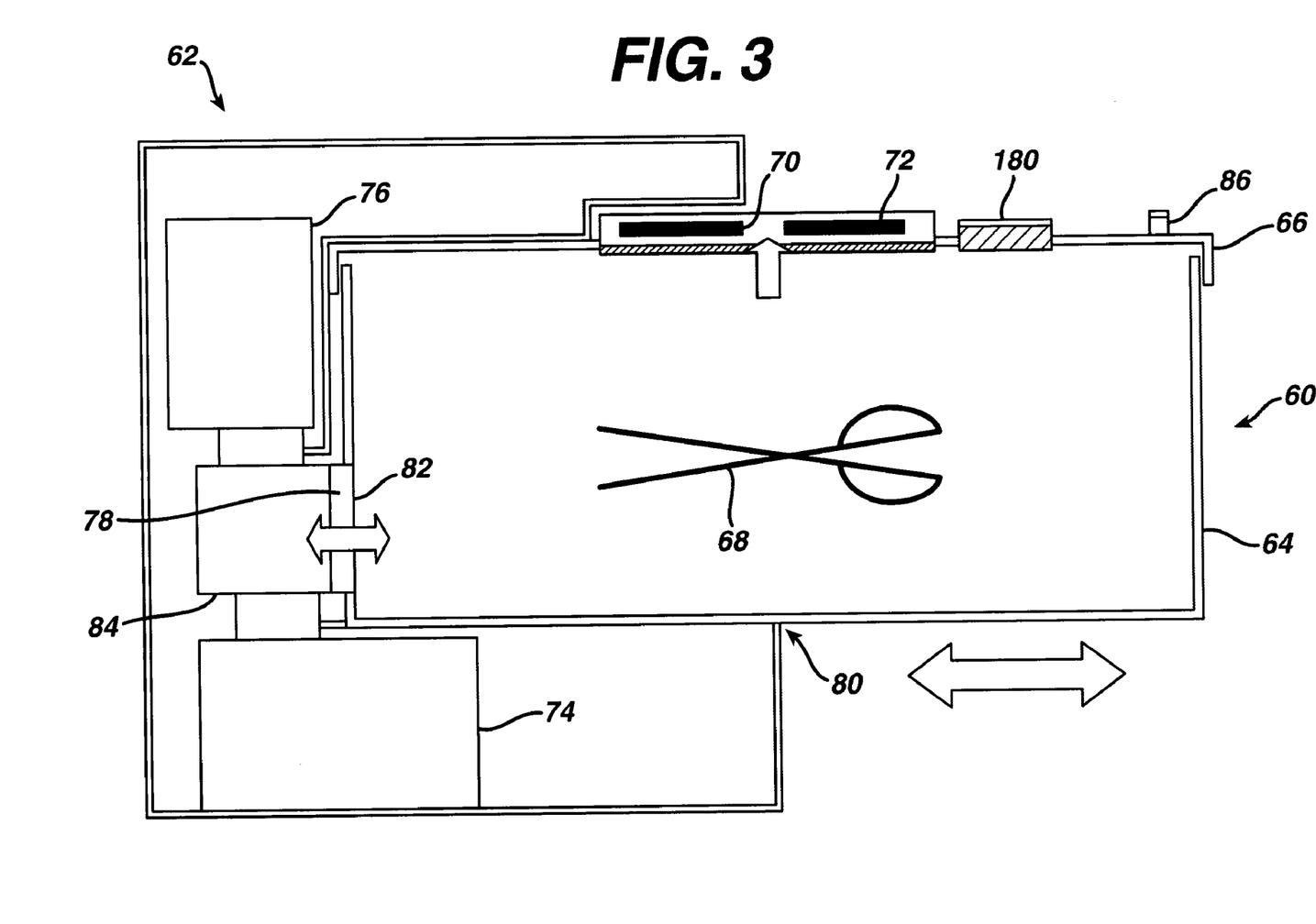
FIG. 3 is a block diagram of a sterilization container according to the present invention connected to a sterilizer.

FIG. 3 illustrates a third type of container 60 adapted to be connected to a sterilizer 62. The container 60 comprises an enclosure 64 having a lid 66 and containing an instrument 68. The enclosure 64 is preferably formed of a material suitable for use in steam, hydrogen peroxide and ethylene oxide sterilization process, such as a liquid crystal polymer as described in the aforementioned U.S. Pat. No. 6,379,631. Suitable polymers include polybenzoate-naphthalate; polybenzoate-terephthalate-bisphenol-isophthalate; polybenzoateterphthalate-ethylene glycol; and polynaphthalate-amino terephthalate. The biological indicator 70 and chemical indicator 72 are provided as in the previous two containers. The sterilizer 62 comprises a vacuum pump 74 and a source of sterilant 76 which connect via an interface 78 to the container 60.

The sterilizer 62 has a receiving bay 80 for receiving a portion of the container 60. An interface 82 on the container 60 interfaces with the interface 78 on the sterilizer 62 to place the container enclosure 64 into fluid communication with the vacuum pump 74 and sterilant source 76. One or more valves 84 controls the fluid communication between the sterilant source 76 and the interface 78 and also the vacuum pump 74 and the interface 78. A simple sterilization process would involve engaging the container 60 into the receiving bay 80 of the sterilizer 62 and then drawing a vacuum on the enclosure 64 via the vacuum pump 74. Once a sufficient vacuum is established, sterilant from the sterilant source 76 can be admitted into the enclosure 64 either in gaseous, mist, or liquid form and then the unvaporized portion thereof would quickly vaporize due to the vacuum within the enclosure 64. A heated vaporizer (not shown) could be used to enhance the vaporization as the sterilant enters the enclosure 64. After a sufficient period of time the sterilant will effect the sterilization of the instrument 68 and the container 60 can be removed from the receiving bay 80.

The container 60 may either be left under vacuum or have its pressure normalized to atmospheric prior to removal of bay 80. If the vacuum is retained and a manually operated vacuum relief valve 86 is provided, when the operator opens the vacuum relief valve 86 and hears an inrush of air the operator will know that the integrity of the container 60 has not been violated since the time of the sterilization procedure. More efficient sterilization cycles can also be employed in which the vacuum and sterilant admission steps.

Figure 4:
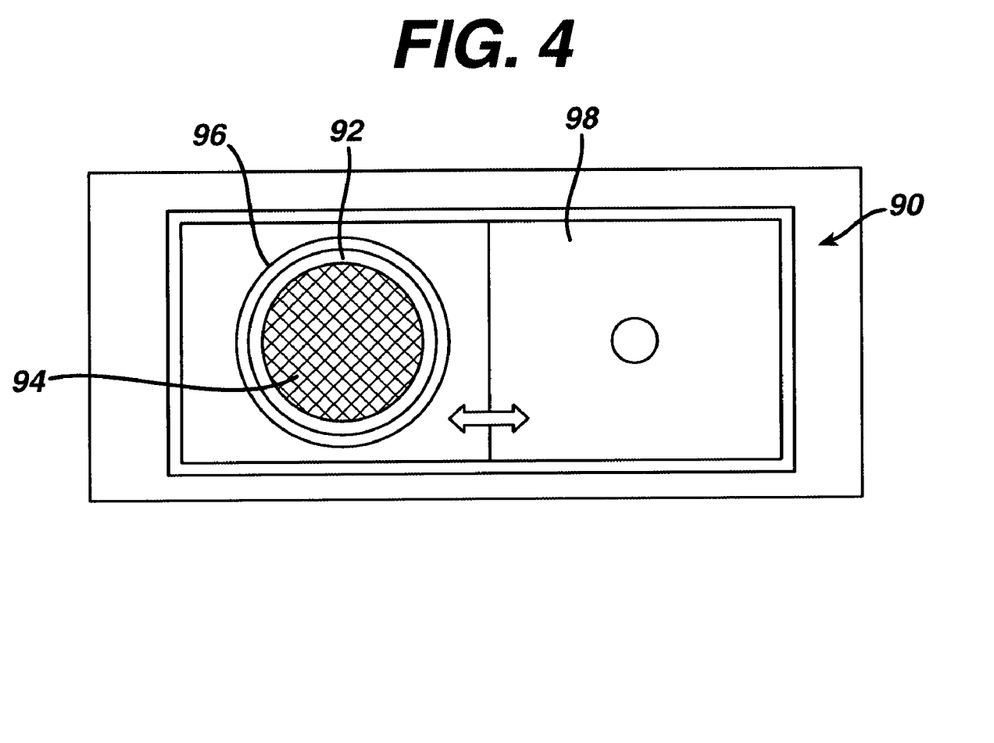
FIG. 4 is a front elevation view of an interface on the container of FIG. 3, shown in an open position.
Figure 5:
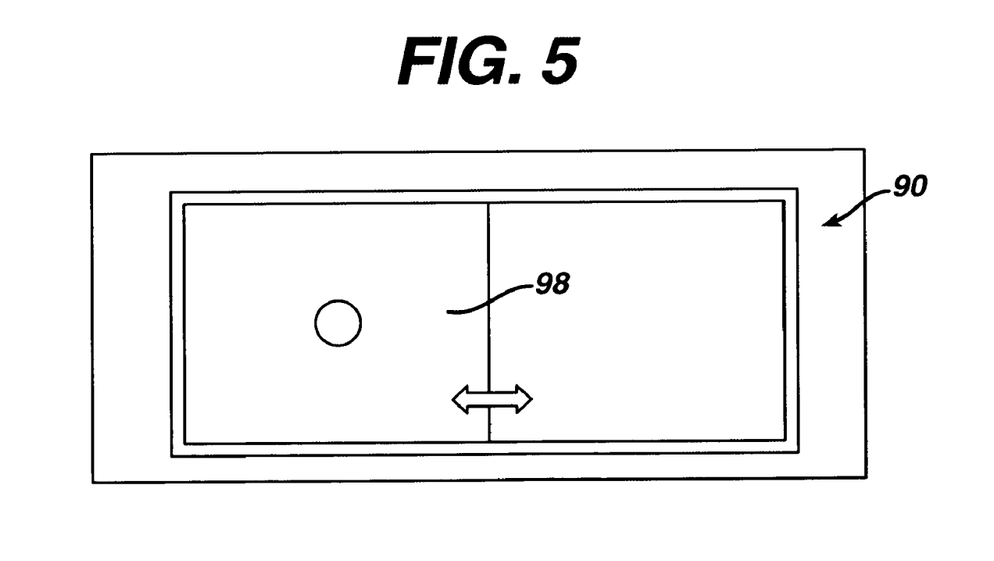
FIG. 5 is a front elevation view of the interface of FIG. 4, shown in a closed position.

Turning also to FIGS. 4 and 5, an interface 90 for the container 60 allows the container 60 to operate effectively in the fashions depicted in FIG. 1, or FIG. 2, or FIG. 3. The interface 90 comprises an aperture 92 into the enclosure 64, the aperture 92 being covered by a semipermeable filter 94 to allow passage of sterilizing media yet disallow passage of potentially contaminating microorganisms. An O-ring or gasket 96 surrounds the aperture 92 to help ensure a pressure tight seal with the interface 78 on the sterilizer 62. To close the aperture 92 for use as depicted in the manner of FIG. 2, a panel 98 slides over the aperture 92 and seals against the O-ring 96, as depicted in FIG. 5.

Figure 6:
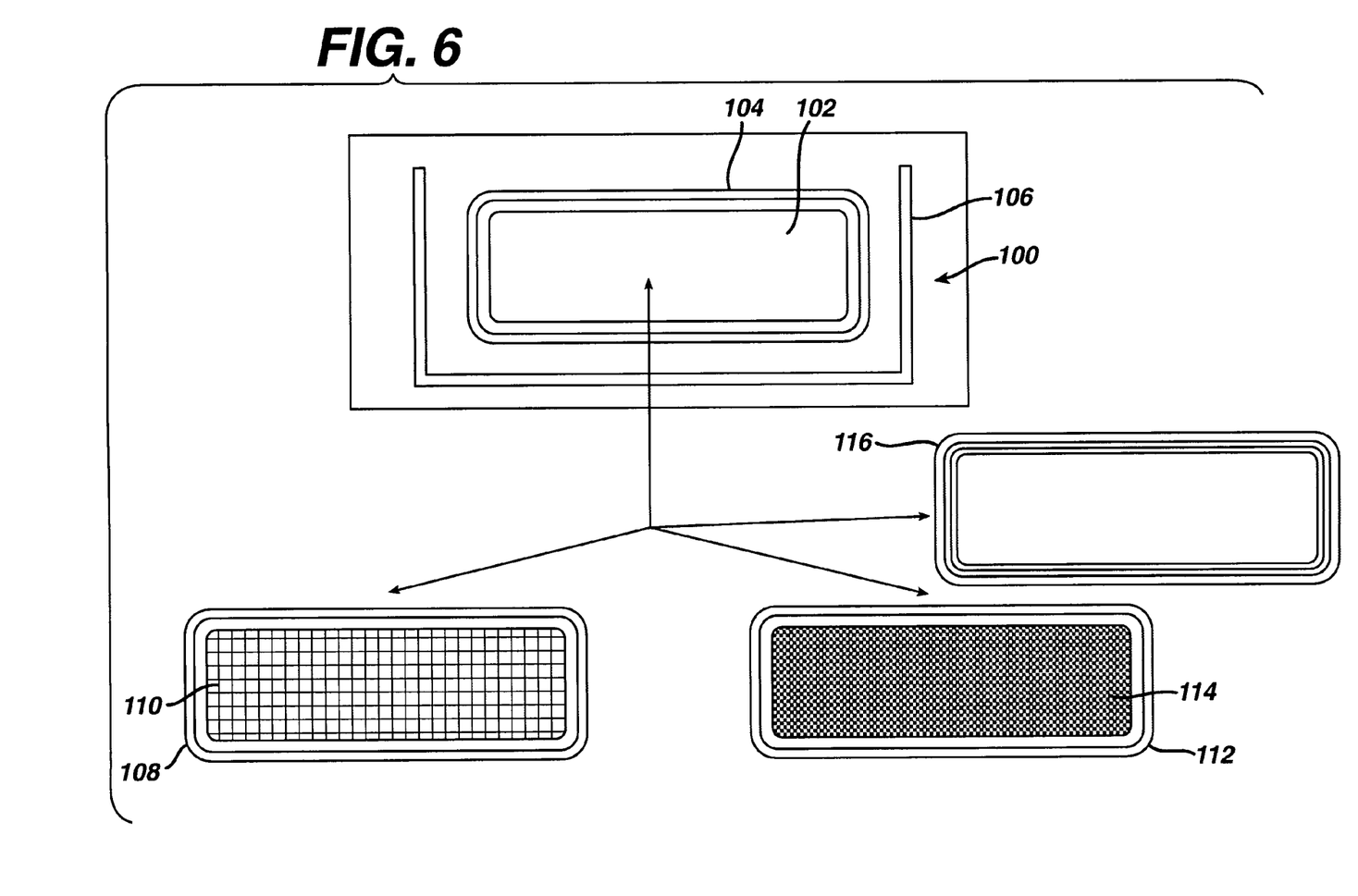
FIG. 6 is a front elevation view of an alternative interface for the container of FIG. 3.

Turning also to FIG. 6, an alternative embodiment of an interface 100 comprises an aperture 102 surrounded by an O-ring or gasket 104 and having a frame 106 to receive various inserts. A first insert 108 fits into the frame 106 and comprises a screen 110 having holes large enough to easily pass a mist of sterilant media into the enclosure 64. A second alternative insert 112 comprises a semipermeable filter 114 for passing vapor phase sterilant media yet disallowing passage of contaminating microorganisms. A third insert 116 comprises merely a solid plate to block the aperture 102 entirely.

The first insert 108 having the screen 110 would be most useful for use with a sterilizer such as the sterilizer 62 in which the sterilant media enters the container 60 as a mist and in which the instruments 68 will not be stored in the container 60 after the procedure but rather will be used immediately thereafter, or where such instruments do not require complete sterility after the procedure. For instance, if the instruments 68 are dental instruments, a high level of sterilization efficiency may be desirable to kill difficult pathogens from a prior patient, but after the sterilization it would be acceptable to store the instruments in a clean environment yet not in a bacteria proof enclosure.

The second insert 112 would be useful when the sterilizer 62 admits vapor phase sterilant into the container 60, and would also be useful in the sterilizer depicted in FIG. 1 where the container 60 would be placed into a sterilization chamber 20.

The third insert 116 would primarily be useful when the container is used as a self-contained sterilization container as in the manner depicted in FIG. 2.

Figure 7:
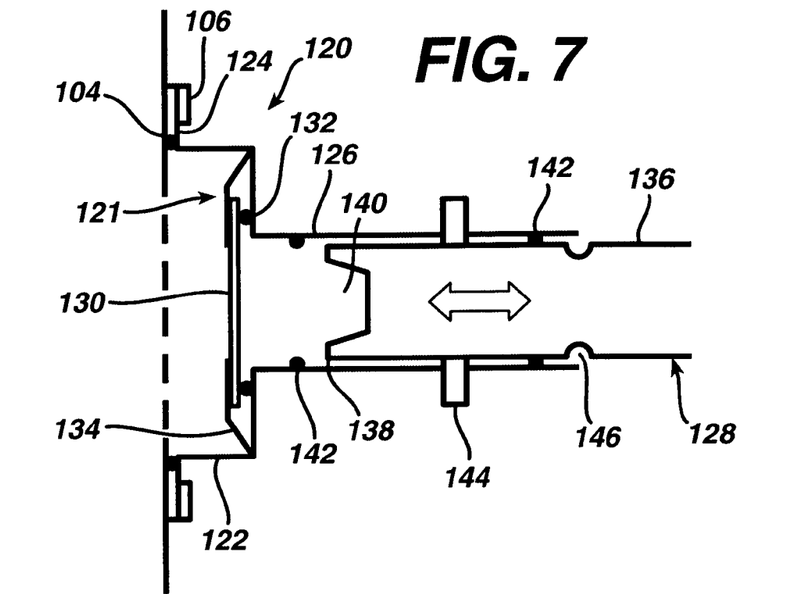
FIG. 7 is a cut-away view of an insert for the interface of FIG. 6 and having a self-closing mechanism shown in the closed position.
Figure 8:
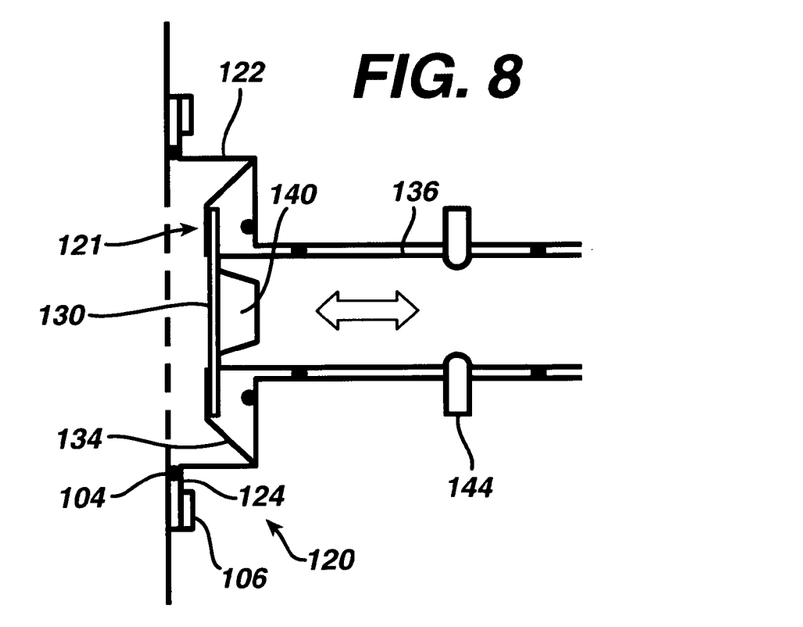
FIG. 8 is a cut-away view of the insert of FIG. 7, shown in the open position.

Turning also to FIGS. 7 and 8, an alternative insert 120 fits into the frame 106 and is primarily useful when employing a mist form of the sterilization media in the sterilizer 62 combined with the need to store the instruments 68 in the container 60 in a sterile form after the sterilization process is complete. The insert 120 employs a self-closing mechanism 121 which opens upon insertion of the container 60 into the sterilizer 62 to allow introduction of mist into the enclosure 64 and which closes automatically upon removal of the sterilization container 60 from the sterilizer 62 to seal the enclosure 64 from potentially contaminating microorganisms. The insert 120 comprises a body 122 having a flange 124 which fits into the frame 106 and seals against the O-ring or gasket 104. An open tube 126 extends outwardly from the body 122 to receive an adapter 128 from the sterilizer interface 78. The body 122 contains the self-closing mechanism 121. It comprises a valve member 130 biased toward a valve seat 132 on the body by a spring 134 or other biasing member. When seated on the valve seat 132 the valve member 130 seals the body 122 from the tube 126, thus effectively sealing the container aperture 102.

The adapter 128 comprises a pipe 136 having a distal end 138 that abuts the valve member 130 driving it away from the valve seat 132. One or more openings 140 of some form at or near the pipe distal end 138 place the pipe 136 into fluid communication with the body 122 and thus with the enclosure 64. Seals 142 provide a tight seal between the pipe 136 and tube 126. Spring loaded members 144 engage detents 146 on the pipe 136 to hold it in place. Upon removal of the container 60 from the bay 80 the pipe 136 will disengage from the valve member 130 and close the self-closing mechanism 121.

The mechanism of FIG. 7 relies upon the enclosure 64 to be near or above ambient pressure to keep the self-closing mechanism 121 closed. With a pressure slightly above ambient, opening of the relief valve 84 (FIG. 3) still causes an audible air rush to alert a user to the integrity of the container's seal.

Figure 9:
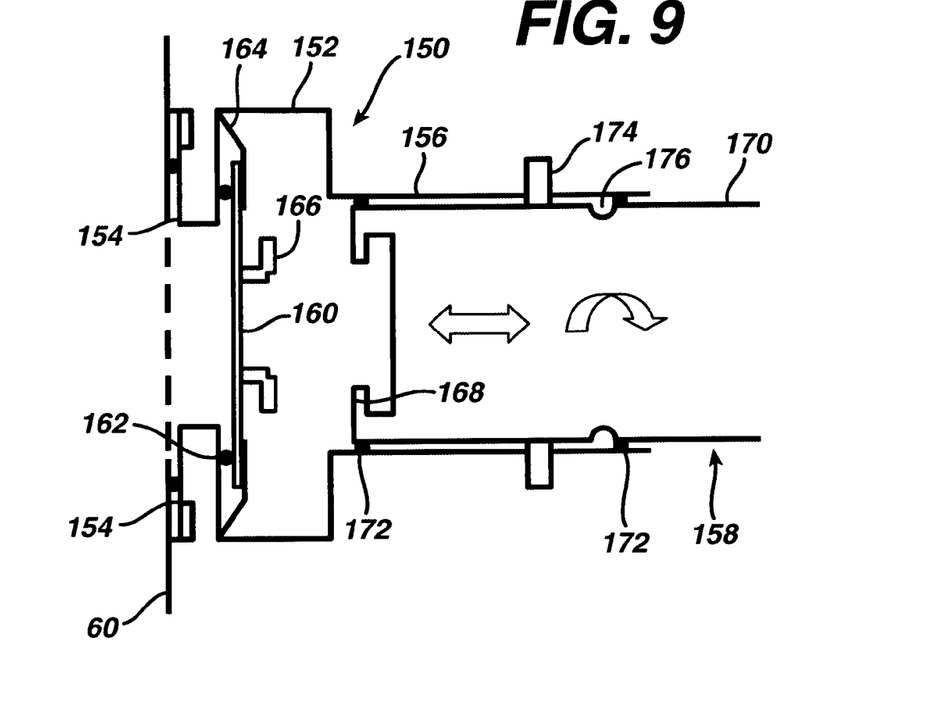
FIG. 9 is a cut-away view of an alternative insert for the interface of FIG. 6 and having a self-closing mechanism, shown in the closed position.
Figure 10:
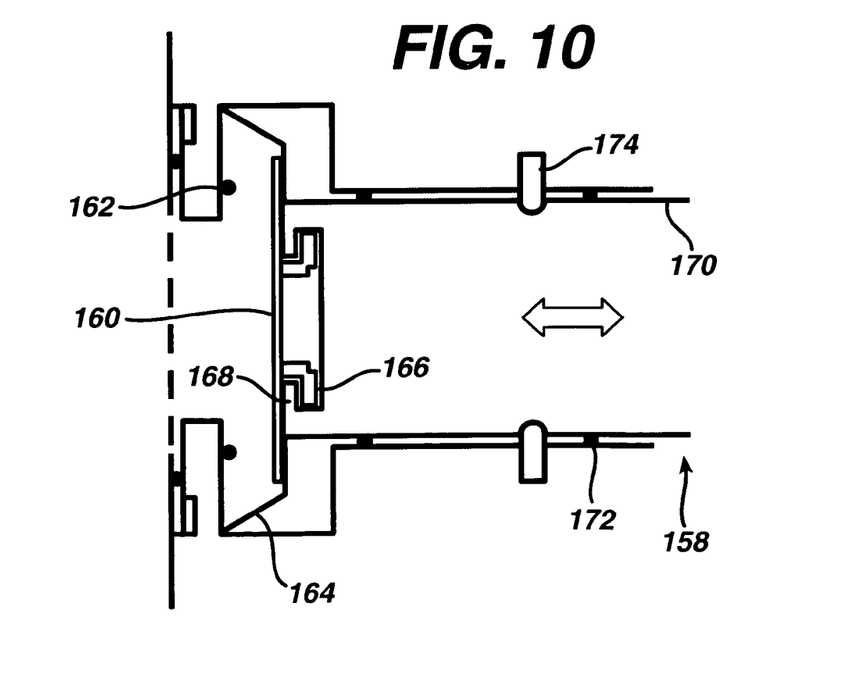
FIG. 10 is a cut-away view of the insert of FIG. 9, shown in the open position.

Turning to FIGS. 9 and 10, if a vacuum is desired for storage of the container 60, an alternative insert 150 may be used. It comprises a body 152 and flange 154 for connection to the container 60 and a tube 156 for receiving an adapter 158 from the sterilizer 62 (not shown in FIGS. 9 and 10). The body 152 contains a valve member 160 biased toward a valve seat 162 by a biasing member 164. However, it differs from the previous embodiment in that it closes toward the container 60, such that a vacuum in the container 60 holds the valve member 160 closed. A flange 166 on the valve member 160 engages a flange 168 on a pipe 170 of the adapter 158. The pipe 170 rotates to engage the flanges 166 and 168 with each other and is then retracted slightly to pull the valve member 160 away from the valve seat 162. Seals 172 are provided between the pipe 170 and tube 156. Spring loaded members 174 engage detents 176 on the pipe 170 to hold the parts in the proper orientation. After the sterilization process the process is reversed to seat the valve member 160.

While the provision of various inserts 108, 112, 116, 120 and 150 provides the most flexibility, either of the inserts 120 or 150 could be integral with the container rather than removable to nevertheless provide the container with the ability to be used interchangeably in the processes of FIG. 1 and FIG. 2 and FIG. 3.

Further, to enhance its flexibility, the container 60 may include multiples of the features disclosed herein. For instance, especially when configured with the inserts 120 and 150 with their self-closing feature it is preferred to have, especially at the top and bottom of the container 60 (best seen in FIG. 3), additional filtered ports 180 which may be sealed. Such ports could be similar to the interface 90, or could have screw-on covers or other sealing mechanisms. Preferably, the filters can be replaced, as is preferable with any of the filters discussed herein. Such additional ports provide enhanced diffusion of sterilant into and out of the container 60 when used in a standard chamber 20 such as disclosed in FIG. 1. When used in the process of FIG. 3 the ports 180 would be left closed.

Figure 11:
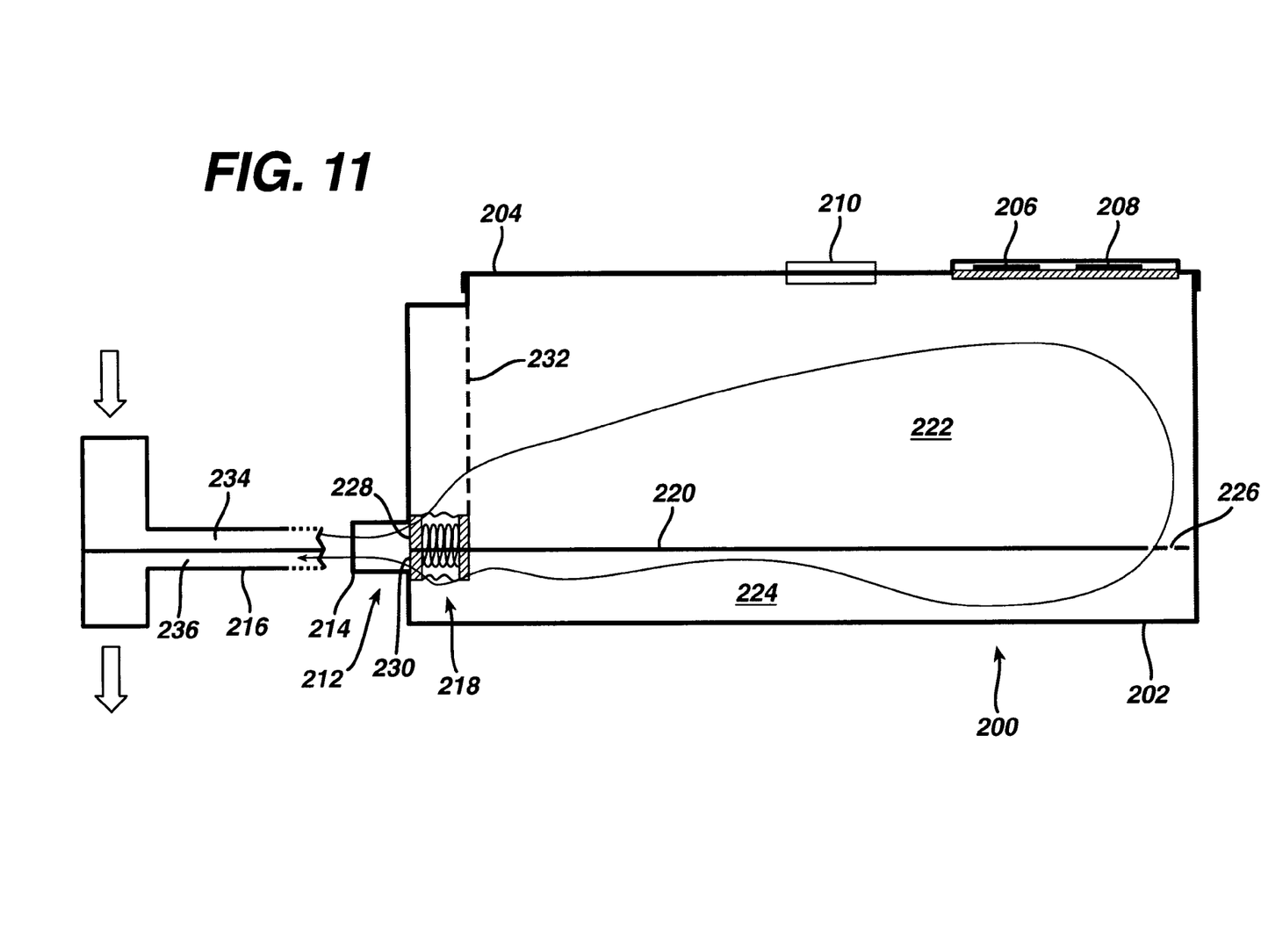
FIG. 11 is a cut-away view of an alternative embodiment of a sterilization container according to the present invention.

FIG. 11 discloses an alternative embodiment of a container 200, especially useful in the sterilizer 62 of FIG. 3, but offering enhanced flow through the container 200. It comprises an enclosure 202 having a lid 204, provision for a biological indicator 206 and chemical indicator 208 and a sealable filtered port 210 in the lid 204. An inlet/exit port 212 has an opening 214 for receiving a probe 216 from the sterilizer 60. A normally closed spring loaded valve 218 opens when the probe 216 is inserted into the opening 214 and abuts the valve 218. A solid partition 220 separates the enclosure 202 into an upper portion 222 and lower portion 224. A filtered aperture 226 in the partition, away from the port 212, connects the upper and lower portions 222 and 224. The opening 214 is partitioned into an upper path 228 and lower path 230. A filtered partition 232 separates the upper portion 222 from the upper path 228 and the lower path 230 communicates with the lower portion 224. The probe 216 is preferably similarly separated into an upper path 234 adapted to communicate with the opening upper path 228 and a lower path 236 adapted to communicate with the port lower path 230.

When the probe 216 enters the opening 214 it opens the valve 218. Sterilizing media gases flow in from the probe upper path 234 into the opening upper path 228 and into the enclosure upper portion 222. These gases exit the enclosure 202 by flowing through the filtered aperture 226 into the enclosure lower portion 224 and out through the opening and probe lower paths 230 and 236. After the probe 216 is removed, the spring loaded valve 218 closes and seals the enclosure 202. Instruments for sterilization, which were placed into the upper portion 222 through the lid 204, and are now sterile, are further protected from contamination by the filtered aperture 226 and filtered partition 232 which will block ingress of potentially contaminating microorganisms even if the spring loaded valve 218 were to leak.

Figure 12:
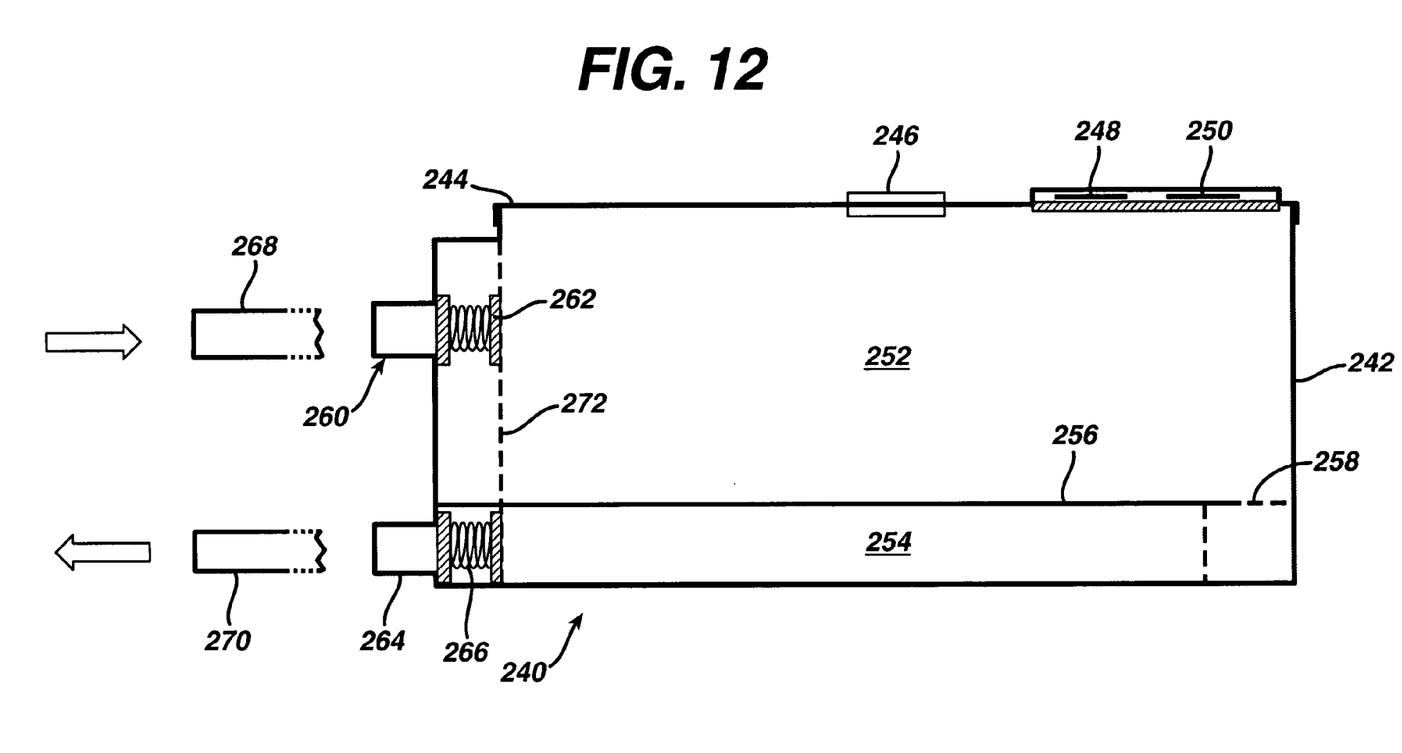
FIG. 12 is a cut-away view of a further alternative embodiment of a sterilization container according to the present invention.

FIG. 12 illustrates a similar container 240 comprising an enclosure 242 having a lid 244, a filtered port 246 and provisions for a biological indicator 248 and chemical indicator 250. The enclosure 242 is separated into an upper portion 252 and lower portion 254 by a solid partition 256 having a filtered aperture 258. The container 240 has an inlet port 260 into the upper portion 252, with a spring-loaded valve 262 and an exit port 264 from the lower portion 254, also with a spring-loaded valve 266. The inlet port 260 receives an inlet probe 268 and the exit port 264 receives an exit probe 270. A filter 272 separates the inlet port 260 from the upper portion 252. Gases flow from the inlet probe 268 into the enclosure upper portion 252 and exit from the exit probe 270 as in the previous embodiment. To allow for flow through of mist based sterilants, such as a solution of hydrogen peroxide, the filter 272 can be replaced by a screen and the aperture 258 need not be filtered. The valves 262 and 266 will protect the integrity of the enclosure 242 post sterilization.

The flow could be continuous, in which case it would be desireable to continually recirculate the same sterilant through the enclosure 242. Alternatively, the exit probe 270 can be used to exhaust the atmosphere in the enclosure 242 to a vacuum as low as 0.5 torr (depending upon the strength of the enclosure 242 and the vacuum pump) and then the inlet probe 268 can, especially in connection with a heated vaporizer, supply sterilant such as hydrogen peroxide vapor to the enclosure 242. After a sufficient time to effect sterilization, the exit probe 270 can draw out the sterilant.

One of skill in the art will recognize that the location of the ports 260 and 264 can be changed to address other functional needs while keeping with the concept of flowing gases more efficiently through the container 240. For instance, they could be located on the bottom of the container with suitable partitioning within the enclosure 242 to route incoming gases to the enclosure upper portion 252. Rather than have spring-loaded valve 262 and 266 which move directly away from the incoming probes 268 and 270, spring-loaded flap valves (not shown) which rotate away from the incoming probe could be substituted therefor and would not tend to push the probe out after its insertion.

While the invention has been particularly described in connection with specific embodiments thereof, it is to be understood that this is by way of illustration and not of limitation, and that the scope of the appended claims should be construed as broadly as the prior art will permit.

What is claimed is:

1. A sterilization container kit for sterilizing, transporting and storing one or more medical instruments, comprising:
    an enclosure defining an interior space adapted to house the one or more medical instruments, said enclosure sealed against the ingress of contaminating microorganisms;
    an opening into the enclosure having associated therewith an adapter;
    a set of inserts attachable to the adapter, the set comprising:
        a cover for blocking the opening;
        a filter for covering the opening, the filter being permeable to vapor phase sterilants and impermeable to contaminating microorganisms; and
        a self closing valve:
    wherein the self closing valve comprises a seat at the opening and a closing member engageable with the seat wherein when the closing member is engaged with the seat the closing member blocks fluid communication between the interior space and an environment exterior of the enclosure through the opening and wherein the self closing valve closure further comprises a biasing member urging the closing member toward the seat; and
    wherein the self-closing valve further comprises an inlet for receiving a projecting member from a source of sterilant, the closing member being positioned with respect to the inlet such that when the projecting member is inserted into the inlet the projecting member abuts the closing member and moves it away from the seat.

2. A sterilization container kit according to claim 1 wherein the adapter comprises a flange about the opening into which fits one of the inserts.

3. A sterilization container kit according to claim 1 and further comprising a seal surrounding the opening.

4. A sterilization container kit according to claim 1 and further comprising an instrument holder within the enclosure.

5. A sterilization container kit according to claim 1 and further comprising one or more apertures into the enclosure which are capable of being sealed.

6. A sterilization container kit according to claim 1 and further comprising a pressure release valve.

7. A sterilization container kit according to claim 1 wherein the enclosure is formed of a liquid crystal polymer.

8. A sterilization container according to claim 1 and further comprising an instrument opening into the enclosure for placing the one or more medical instruments therein and a lid for the instrument opening.

9. A sterilization container according to claim 1 wherein the set further comprises a screen.

10. A sterilization container for sterilizing, transporting and storing one or more medical instruments, comprising:
    an enclosure defining an interior space adapted to house the one or more medical instruments, said enclosure sealed against the ingress of contaminating microorganisms;
    an opening into the enclosure having associated therewith an adapter;
    a set of inserts attachable to the adapter, the set comprising:

a cover for blocking the opening;
a filter for covering the opening, the filter being permeable to vapor phase sterilants and impermeable to contaminating microorganisms; and
a self closing valve
wherein the self closing valve comprises a seat at the opening and a closing member engageable with the seat wherein when the closing member is engaged with the seat the closing member blocks fluid communication between the interior space and an environment exterior of the enclosure through the opening and wherein the self closing valve closure further comprises a biasing member urging the closing member toward the seat; and
wherein the self-closing valve comprises an inlet for receiving a projecting member from a source of sterilant, the closing member having thereon a first flange engageable by a second flange on the projecting member whereby movement of the projecting member relative to the inlet moves the closing member.

* * * * *